United States Patent
Meglan

(10) Patent No.: US 10,251,672 B2
(45) Date of Patent: Apr. 9, 2019

(54) METHODS AND APPARATUS FOR CONTROLLING SURGICAL INSTRUMENTS USING A SURGICAL PORT ASSEMBLY

(71) Applicant: Covidien LP, Mansfield, MA (US)

(72) Inventor: Dwight Meglan, Westwood, MA (US)

(73) Assignee: Covidien LP, Mansfield, MA (US)

( * ) Notice: Subject to any disclaimer, the term of this patent is extended or adjusted under 35 U.S.C. 154(b) by 162 days.

(21) Appl. No.: 15/520,966

(22) PCT Filed: Oct. 13, 2015

(86) PCT No.: PCT/US2015/055226
§ 371 (c)(1),
(2) Date: Apr. 21, 2017

(87) PCT Pub. No.: WO2016/064617
PCT Pub. Date: Apr. 28, 2016

(65) Prior Publication Data
US 2018/0021062 A1    Jan. 25, 2018

Related U.S. Application Data

(60) Provisional application No. 62/067,698, filed on Oct. 23, 2014.

(51) Int. Cl.
*A61B 17/34* (2006.01)
*A61B 90/00* (2016.01)
(Continued)

(52) U.S. Cl.
CPC ...... *A61B 17/3439* (2013.01); *A61B 17/3423* (2013.01); *A61B 34/35* (2016.02); *A61B 90/37* (2016.02); *A61B 1/05* (2013.01); *A61B 34/70* (2016.02); *A61B 90/361* (2016.02); *A61B 2017/00199* (2013.01); *A61B 2017/00557* (2013.01); *A61B 2017/00858* (2013.01)

(58) Field of Classification Search
CPC .. A61B 17/3439; A61B 34/35; A61B 17/3423
See application file for complete search history.

(56) References Cited

U.S. PATENT DOCUMENTS 3,788,318 A * 1/1974 Kim .................. A61M 5/00
                                                   604/104
5,803,921 A    9/1998 Bonadio
(Continued)

FOREIGN PATENT DOCUMENTS

WO    2013084107 A2    6/2013

OTHER PUBLICATIONS

International Search Report for (PCT/US2015/055226) date of completion is Jan. 13, 2016 (6 pages).
(Continued)

*Primary Examiner* — Christian Sevilla

(57) ABSTRACT

The present disclosure relates to surgical port assemblies including a plurality of inflatable members for applying a force to a portion of a shaft of a surgical instrument which is inserted through an interior space of the surgical port assembly, and to surgical systems including a surgical port assembly, an endoscopic camera, and a control mechanism for controlling inflation and deflation of the plurality of inflatable members of the surgical port assembly.

16 Claims, 7 Drawing Sheets

(51) Int. Cl.
 *A61B 34/35* (2016.01)
 *A61B 17/00* (2006.01)
 *A61B 34/00* (2016.01)
 *A61B 1/05* (2006.01)

(56) References Cited

U.S. PATENT DOCUMENTS

| | | | |
|---|---|---|---|
| 6,238,373 | B1 | 5/2001 | De La Torre et al. |
| 6,679,836 | B2 | 1/2004 | Couvillon, Jr. |
| 8,641,610 | B2 | 2/2014 | Okoniewski et al. |
| 8,696,557 | B2 | 4/2014 | Fishchvogt |
| 2004/0154624 | A1* | 8/2004 | Bonadio ............ A61B 17/0293 128/849 |
| 2005/0085693 | A1 | 4/2005 | Belson et al. |
| 2005/0124980 | A1 | 6/2005 | Sanders |
| 2005/0283203 | A1 | 12/2005 | Flaherty et al. |
| 2006/0247498 | A1 | 11/2006 | Bonadio et al. |
| 2007/0038224 | A1 | 2/2007 | Ortiz |
| 2007/0265502 | A1 | 11/2007 | Minosawa et al. |
| 2009/0275823 | A1 | 11/2009 | Ayati et al. |
| 2010/0288282 | A1 | 11/2010 | Brewer et al. |
| 2010/0312065 | A1* | 12/2010 | Shelton, IV ....... A61B 17/3423 600/207 |
| 2011/0251462 | A1 | 10/2011 | Rockrohr |
| 2012/0116416 | A1 | 5/2012 | Neff et al. |
| 2012/0157780 | A1* | 6/2012 | Okoniewski ....... A61B 17/3423 600/207 |
| 2013/0053783 | A1 | 2/2013 | Szweda et al. |
| 2013/0274788 | A1* | 10/2013 | Jennings ............ A61B 17/0231 606/191 |
| 2014/0039375 | A1* | 2/2014 | Jimenez .................. A61F 2/064 604/9 |
| 2016/0008081 | A1* | 1/2016 | Forsell ............... A61B 17/3423 600/204 |
| 2016/0089181 | A1 | 3/2016 | Johnson |

OTHER PUBLICATIONS

Extended European Search Report corresponding to counterpart EP Patent Appln. 15 85 3257.2 dated Jul. 2, 2018.

* cited by examiner

METHODS AND APPARATUS FOR CONTROLLING SURGICAL INSTRUMENTS USING A SURGICAL PORT ASSEMBLY

CROSS-REFERENCE TO RELATED APPLICATIONS

This application is a U.S. National Stage Application filed under 35 U.S.C. § 371(a) of International Patent Application Serial No. PCT/US2015/055226, filed Oct. 13, 2015, which claims the benefit of and priority to U.S. Provisional Patent Application Ser. No. 62/067,698, filed Oct. 23, 2014, the entire disclosure of which is incorporated by reference herein.

BACKGROUND OF RELATED ART

Surgical techniques and instruments have been developed that allow a surgeon to perform an increasing range of surgical procedures with minimal incisions into the skin and body tissue of a patient. Minimally-invasive surgery has become widely accepted in many medical specialties, often replacing traditional open surgery. Unlike open surgery, which typically requires a relatively large incision, minimally-invasive procedures, such as endoscopy or laparoscopy, are performed through one or more relatively small incisions.

In laparoscopic and endoscopic surgical procedures, a small "keyhole" incision or puncture is typically made in a patient's body, e.g., in the abdomen, to provide an entry point for a surgical access device which is inserted into the incision and facilitates the insertion of specialized instruments used in performing surgical procedures within an internal surgical site. The number of incisions may depend on the type of surgery. It is not uncommon for some abdominal operations, e.g., gallbladder surgery, to be performed through a single incision. In most patients, the minimally-invasive approach leads to decreased post-operative pain, a shorter hospital stay, a faster recovery, decreased incidence of wound-related and pulmonary complications, cost savings by reducing post-operative care, and, in some cases, a better overall outcome.

Minimally-invasive surgical procedures are performed throughout the body and generally rely on obtaining access to an internal surgical site through a relatively small pathway, often less than one centimeter in diameter. One method of providing such a pathway is by inserting a trocar assembly through the skin of a patient. Commonly, to place the trocar assembly, the penetrating tip of the obturator of the trocar is pushed through the skin and underlying tissue until the distal end of the cannula is within the body cavity. Alternatively, some trocar devices have a blunt obturator tip for placing the cannula through a previously-made incision, for example. Once the trocar has been properly positioned, the obturator is removed and the cannula is then available as a pathway between the surgical site and the exterior of the patient's body through which the surgeon may introduce the various surgical instruments required to perform the desired procedures. Surgical instruments insertable through a cannula include forceps, clamps, scissors, probes, flexible or rigid scopes, staplers and cutting instruments.

In some procedures, a wall of a body cavity is raised by pressurization of the body cavity to provide sufficient working space at the surgical worksite and/or to allow a trocar to penetrate the body cavity without penetrating an organ within the cavity. The process of distending the abdomen wall from the organs enclosed in the abdominal cavity is referred to as insufflation. During a laparoscopic procedure (endoscopy in the abdominal cavity), insufflation may be achieved by introducing an insufflation gas, such as carbon dioxide, nitrogen, nitrous oxide, helium, argon, or the like, through a Veress needle or other conduit inserted through the abdominal wall, to enlarge the area surrounding the target surgical site to create a larger, more accessible work area. The surgeon is then able to perform the procedure within the body cavity by manipulating the instruments that have been extended through the surgical access device(s). The manipulation of such instruments within the internal body is limited by both spatial constraints and the need to maintain the body cavity in an insufflated state.

In minimally-invasive surgery, the surgeon does not have direct visualization of the surgical field, and thus minimally-invasive techniques require specialized skills compared to corresponding open surgical techniques. Although minimally-invasive techniques vary widely, surgeons generally rely on a lighted camera at the tip of an endoscope to view the surgical site, with a monitor displaying a magnified version of the site for the surgeon to use as a reference during the surgical procedure. The surgeon then performs the surgery while visualizing the procedure on the monitor. The camera is typically controlled by an assistant to the surgeon. In many instances, the assistant does not play any other role in the procedure other than to hold and direct the camera so that the surgeon can view the surgical site. The assistant may have difficulty understanding the surgeon's intent, requiring the surgeon either to move the camera himself or ask the assistant to redirect the camera.

Multi-function robotic surgical systems are available with laparoscopic camera control. In general, robotic surgical systems are large and bulky, requiring a large amount of space around the patient, and have complex, time-consuming setups. Extensive training time is typically required for surgeons to learn to operate the remotely-controlled, camera-toting devices, and additional specialized training is also typically required for the entire operating room team. The extremely high initial cost of purchasing a robotic surgical system as well as the relatively high recurring costs of the instruments and maintenance can make it prohibitive for many hospitals and health-care centers to invest in such systems.

SUMMARY

The present disclosure relates to surgical port assemblies including a plurality of inflatable members for applying a force to a portion of a shaft of a surgical instrument which is inserted through an interior space of the surgical port assembly, and to surgical systems including a surgical port assembly, an endoscopic camera, and a control mechanism for controlling inflation and deflation of the plurality of inflatable members of the surgical port assembly.

According to an aspect of the present disclosure, surgical port assembly for use with surgical instruments, is provided. The surgical port assembly includes a body and a control interface. The body includes an exterior surface and an interior surface. The interior surface defines an interior space, which is configured to allow a surgical instrument to pass therethrough. The control interface includes a plurality of inflatable members coupled to the body and inflatable to selectively apply a force to a portion of a shaft of the surgical instrument when the shaft is disposed within the interior space. Each of the plurality of inflatable members is independently selectively inflatable to move a distal portion of the surgical instrument to a desired position In disclosed embodiments, at least one of the plurality of inflatable members is configured to apply a force to the endoscopic instrument in a direction perpendicular to a longitudinal axis of the body.

Additionally, the disclosure includes embodiments where the plurality of inflatable members includes nine inflatable members. It is further disclosed that the nine inflatable members include a first set of three axially-aligned inflatable members, a second set of three axially-aligned inflatable members, and a third set of three axially-aligned inflatable members. It is further disclosed that the nine inflatable members include a first set of three radially-aligned inflatable members, a second set of three radially-aligned inflatable members, and a third set of three radially-aligned inflatable members.

In disclosed embodiments, at least one of the plurality of inflatable members includes a friction-enhancing material. It is further disclosed that a majority of each inflatable member is made from a first material, and that the friction-enhancing material is different from the first material.

The present disclosure also relates to a surgical system including a surgical port assembly, an endoscopic camera, and a control mechanism. The surgical port assembly includes a body and a control interface. The body includes an exterior surface and an interior surface, which defines an interior space configured to allow a surgical instrument to pass therethrough. The control interface includes a plurality of inflatable members coupled to the body and inflatable to selectively apply a force to a portion of a shaft of the surgical instrument when the shaft is disposed within the interior space. Each of the plurality of inflatable members is independently selectively inflatable to move a distal portion of the surgical instrument to a desired position. A portion of the endoscopic camera is positionable within a body cavity and configured to view the distal portion of the endoscopic instrument. The control mechanism is disposed in operative engagement with the surgical port assembly and the endoscopic camera, and is configured to control inflation and deflation of the plurality of inflatable members.

It is further disclosed that the control mechanism is configured to control inflation and deflation of each the plurality of inflatable members in response to information received from the endoscopic camera.

Embodiments of the system of the present disclosure also include an inflation medium disposed in fluid communication with each of the plurality of inflatable members individually. It is further disclosed that the inflation medium is disposed in operative communication with the control mechanism.

In disclosed embodiments of the system, at least one of the plurality of inflatable members includes a friction-enhancing material. It is further disclosed that a majority of each inflatable member is made from a first material, and wherein the friction-enhancing material is different from the first material.

It is further disclosed that the plurality of inflatable members includes nine inflatable members. It is further disclosed that the nine inflatable members include a first set of three axially-aligned inflatable members, a second set of three axially-aligned inflatable members, and a third set of three axially-aligned inflatable members. Additionally, it is disclosed that the nine inflatable members include a first set of three radially-aligned inflatable members, a second set of three radially-aligned inflatable members, and a third set of three radially-aligned inflatable members.

BRIEF DESCRIPTION OF THE DRAWINGS

Embodiments of the present disclosure are described herein with reference to the accompanying drawings, wherein.

DETAILED DESCRIPTION

Figure 1:
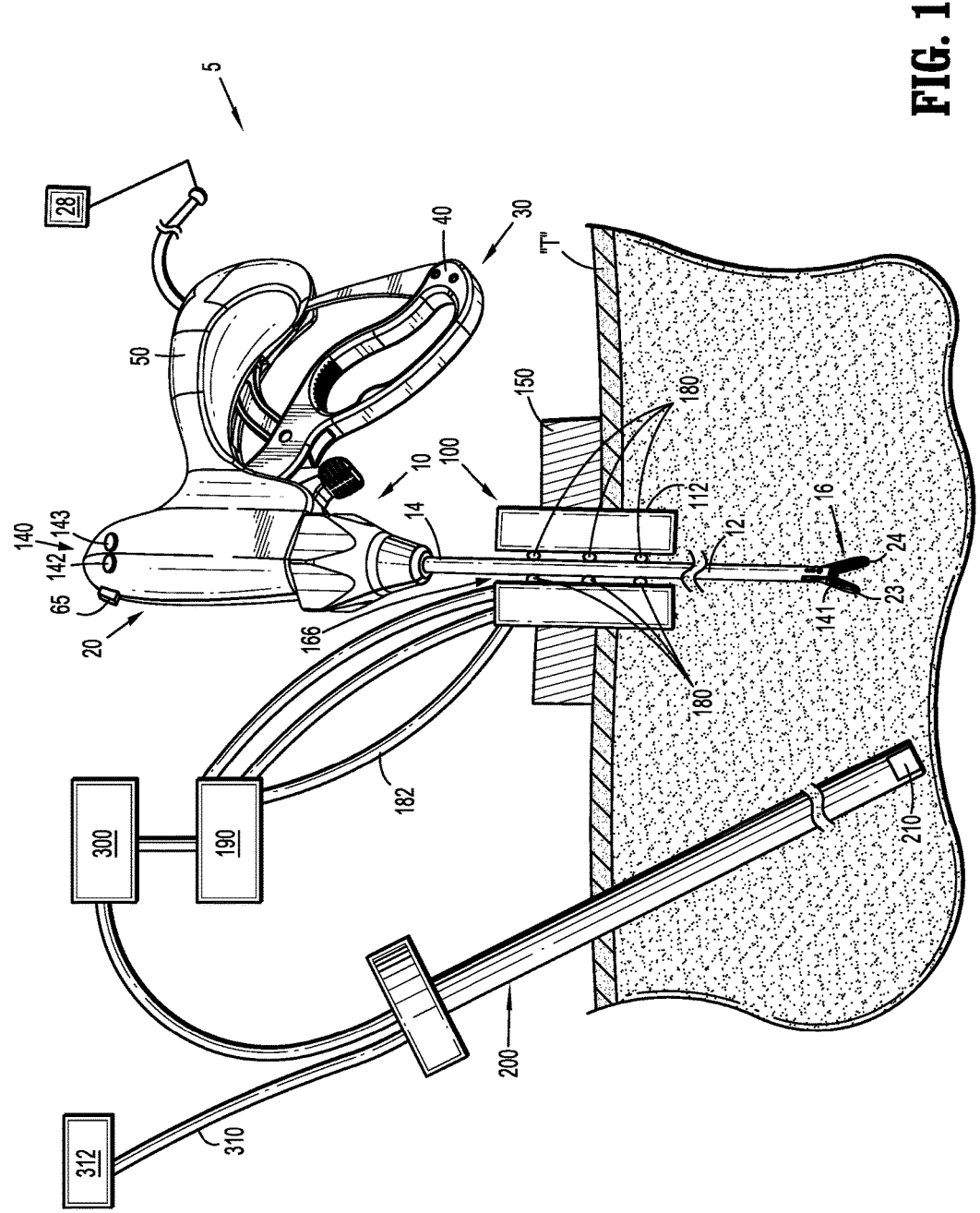
FIG. 1 is a schematic diagram of a system including a port assembly positioned partially within a patient, a surgical instrument positioned within the port assembly, and an endoscopic camera positioned within the patient, where the port assembly is in communication with the endoscopic camera, in accordance with embodiments of the present disclosure.

Embodiments of the presently disclosed port assemblies, surgical devices, and systems are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A minimally-invasive procedure may be defined as any procedure that is less invasive than open surgery used for the same purpose. As it is used in this description, "endoscopic surgery" is a general term describing a form of minimally-invasive surgery in which access to a body cavity is achieved through several small percutaneous incisions. While endoscopic surgery is a general term, "laparoscopic" and "thoracoscopic" describe endoscopic surgery within the abdomen and thoracic cavity, respectively.

As it is used in this description, "transmission line" generally refers to any transmission medium that can be used for the propagation of signals from one point to another.

Various embodiments of the present disclosure provide a port assembly adapted to hold and/or control the movement and/or positioning of a surgical instrument inserted therethrough in conjunction with an endoscopic camera. Embodiments of the presently-disclosed port assembly may be suitable for use in laparoscopic procedures as well as other minimally-invasive surgical procedures, for example.

Various embodiments of the present disclosure provide a port assembly wherein control of the movement and/or positioning of a surgical instrument inserted therethrough may be performed manually or automatically depending on the preference of the surgeon. In some embodiments, the surgical instrument or an endoscopic camera may be provided with a user interface including one or more user-actuable controls and a wireless transmitter to provide a communicative link between the user interface and the port assembly, e.g., to allow the surgeon to change the position and/or orientation of the surgical instrument inserted through the port assembly.

During minimally-invasive surgical procedures, the working end of an instrument is frequently located near the anatomical structure of interest and/or the surgical site within the working envelop. In some embodiments, wherein automatic control is employed for controlling the movement and/or positioning of an endoscopic camera or instrument, a sensor and/or transmitter may be disposed in association with the working end of an instrument, e.g., located on the tip of the instrument, and the endoscopic camera may be automatically controlled to "track" the movement of the instrument tip (e.g., align the field of view of the camera with the working end of the instrument) based on one or more signals outputted by the sensor and/or transmitter. In some embodiments, the sensor and/or transmitter may include an attachment mechanism, e.g., an adhesive backing, to allow the surgeon to selectively position the sensor and/or transmitter on a particular instrument and/or at a particular location on a select instrument, e.g., depending on surgeon preference, the type of surgery, etc.

Some examples of instruments used in minimally-invasive procedures include staplers, graspers, cutters, forceps, dissectors, sealers, dividers, and other tools suitable for use in the area of the anatomical structure of interest. The instrument may be a standalone tool suitable for use within a body cavity or external to the patient's body cavity.

In some embodiments, the controls may include an attachment mechanism, e.g., an adhesive backing, to allow the physician to selectively position the controls on a particular instrument and/or at a preferred location on a select instrument. In some embodiments, the capability may be provided to interface with an existing operating-room management system, e.g., using speech recognition technology, to control one or more settings of operating-room equipment. In some embodiments, the port assembly may be a standalone tool that interfaces with any suitable endoscopic camera.

The present disclosure includes a surgical system 5, which includes a surgical instrument 10, a port assembly 100, an endoscopic camera 200, and/or a control mechanism 300.

FIG. 1 illustrates surgical instrument 10 inserted through an embodiment of port assembly 100 according to the present disclosure. A distal portion of surgical instrument 10 is shown within tissue "T" (e.g., adjacent a surgical site). A distal portion of an endoscopic camera 200 is also shown positioned within the tissue "T." Endoscopic camera 200 is positioned such that endoscopic camera 200 can view a distal portion of surgical instrument 10 within the tissue "T."

In FIG. 1, an embodiment of surgical instrument 10 is shown for use with various surgical procedures and generally includes a housing assembly 20, a handle assembly 30, and an end-effector assembly 22. Surgical instrument 10 includes a shaft 12 that has a distal end 16 configured to mechanically engage the end-effector assembly 22 and a proximal end 14 configured to mechanically engage the housing assembly 20. End-effector assembly 22 generally includes a pair of opposing jaw assemblies 23 and 24 pivotably mounted with respect to one another. In various embodiments, actuation of a movable handle 40 toward a fixed handle 50 pulls a drive sleeve (not shown) proximally to impart movement to the jaw assemblies 23 and 24 from an open position, wherein the jaw assemblies 23 and 24 are disposed in spaced relation relative to one another, to a clamping or approximated position, wherein the jaw assemblies 23 and 24 cooperate to grasp tissue therebetween. Although FIG. 1 depicts a particular type of surgical instrument 10 (e.g., an electrosurgical forceps) for use in connection with endoscopic surgical procedures, port assembly 100, endoscopic camera 200, and control mechanism 300 may be used with a variety of instruments, e.g., depending on the type of surgery.

In some embodiments, as shown in FIG. 1, the port assembly 100 is coupled to a holding member 150. Holding member 150 may be adapted to be attachable to a table to provide support for the port assembly 100, e.g., to provide additional stability and/or reduce the weight of the tool on the patient's body.

When a powered surgical instrument is being used, it is envisioned that a transmission line operably connects the surgical instrument 10 to an electrosurgical power generating source 28. Surgical instrument 10 may alternatively be configured as a wireless device or battery-powered. Surgical instrument 10 may include a switch 65 configured to permit the user to selectively activate the surgical instrument 10. When the switch 65 is depressed, electrosurgical energy is transferred through one or more electrical leads (not shown) to the jaw assemblies 23 and 24, for instance.

In some embodiments, as shown in FIG. 1, the surgical instrument 10 includes a user interface 140, which may be adapted to provide a wireless (or wired) communication interface with the control mechanism 300 of the surgical system 5. Additionally, or alternatively, the surgical instrument 10 may include a sensor and/or transmitter 141, e.g., disposed in association with the end effector assembly 22, or component thereof, e.g., jaw assembly 23. Further, the user interface 140 may be associated with the endoscopic camera 200, for example.

User interface 140 may be disposed on another part of the surgical instrument 10 (e.g., the fixed handle 50, etc.) or another location on the housing assembly 20. User interface 140 may include one or more controls (e.g., two controls 142 and 143 shown in FIG. 1), which may include a switch (e.g., push button switch, toggle switch, slide switch) and/or a continuous actuator (e.g., rotary or linear potentiometer, rotary or linear encoder). In some embodiments, the user interface 140 includes a first control (e.g., control 142) adapted to transmit signals indicative of user intent to effect movement of the end effector assembly 22 within the body cavity. User interface 140 may additionally, or alternatively, include a second control (e.g., control 143) adapted to transmit signals indicative of user intent to adjust the tilt angle of the shaft 12.

Further details of a control mechanism, various sensors, and control interfaces are disclosed in U.S. Pat. No. 8,641,610, which issued on Feb. 4, 2014, the entire contents being incorporated by reference herein.

In disclosed embodiments, a multi-functional sensor 210 is disposed in association with a distal portion of endoscopic camera 200. In some embodiments, multi-functional sensor 210 provides illumination and houses a camera chip. It is to be understood that other sensor embodiments may be utilized. Sensor 210 is operably coupled to a power source (e.g., power supply 312 shown in FIG. 1) via a transmission line 310 coupled to the endoscopic camera 200. Wireless transmission of data from sensor 210 is also contemplated by the present disclosure.

With particular reference to FIGS. 2-5, port assembly 100 generally includes a body 110 and a control interface 160.

Body 110 includes an exterior surface 112, an interior surface 114, and an interior space 116 defined by the interior surface 114. In FIGS. 1, 2, 4 and 5, the exterior surface 112 of the body 110 is shown disposed in sealable contact with tissue "T" at an entry site into the patient's body cavity. Body 110 of port assembly 100 is adapted to allow access into the body cavity, e.g., to allow access of at least one surgical instrument 10 through interior space 116, and may include at least one sealing element or mechanism (not explicitly shown in the interest of clarity) to seal the opening into the body cavity in the presence and/or absence of a surgical instrument 10, e.g., to help prevent the escape of insufflation gas. Body 110 may be formed of any suitable material such as a metal, plastic, alloy, composite material or any combination of such materials, for example.

Control interface 160 includes a plurality of inflatable members 180 (e.g., inflatable members 180a-180i shown in FIG. 2) coupled to, or otherwise disposed in association with, the body 110 of port assembly 100.

Each inflatable member 180 is inflatable and deflatable to apply a force (e.g., perpendicular to a longitudinal axis "A" defined by body 110) to a portion of the elongated shaft 12 of the surgical instrument 10 (i.e., when the elongated shaft 12, or portion thereof, is disposed within the interior space 116 as shown in FIGS. 1 and 3-5) to move the elongated shaft 12 and/or end effector assembly 22 of the surgical instrument 10 to a desired position within the body cavity, for example. As shown in FIG. 1, a portion of the elongated shaft 12 may be disposed within the interior space 116 of the body 110 of the port assembly 100, while the end effector assembly 22 is disposed within the body cavity.

Control interface 160 is adapted to controllably move and/or position the elongated shaft 12 of the surgical instrument 10 to effect movement of the end effector assembly 22 within the body cavity. In disclosed embodiments, the control interface 160 is adapted to receive signals from control mechanism 300 (which is schematically illustrated in FIG. 1). Based on the signals received from the control mechanism 300, the control interface 160 may adjust the spatial aspects of the surgical instrument 10 (e.g., by causing inflation/deflation of at least one inflatable member 180) and/or perform other control functions, alarming functions, or other functions in association therewith. Some examples of spatial aspects associated with the surgical instrument 10 that may be adjusted include tilt angle of the elongated shaft 12 relative to longitudinal axis "A," and rotation of the elongated shaft 12 about a longitudinal axis "B" defined by the elongated shaft 12.

Inflatable members 180 are disposed in mechanical cooperation with the interior surface 114 of the body 110 of the port assembly 100. In disclosed embodiments, each inflatable member 180 is independently controllable with respect to the other inflatable members 180. Here, each inflatable member 180 is in fluid communication with an inflation medium 190 via a conduit 182. (For clarity, FIG. 1 illustrates three conduits 182, but any number of conduits 182 may be included, such as the same number of inflatable members 180). Inflation medium 190 includes any suitable gas (e.g., oxygen, etc.) or fluid (e.g., water or saline) that can be transferred to and from inflatable members 180 of the port assembly 100.

The amount, shape, size, arrangement, and orientation of inflatable members 180 are not limited by the examples shown in the accompanying figures. Rather, any amount, shape, size, arrangement, and orientation of inflatable members 180 are contemplated by the present disclosure.

Figure 2:
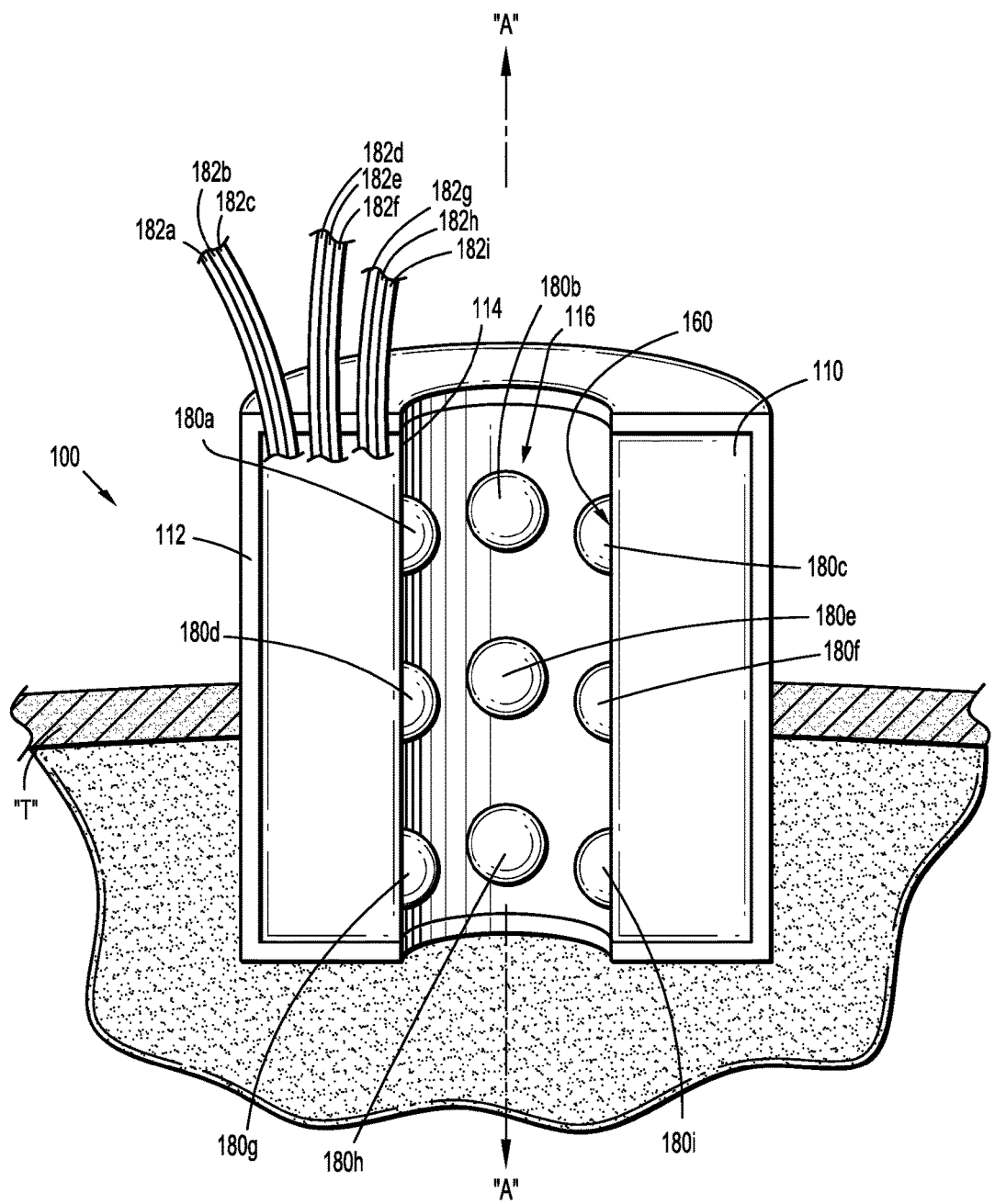
FIG. 2 is a cut-away view of the port assembly of FIG. 1 in accordance with embodiments of the present disclosure.
Figure 3:
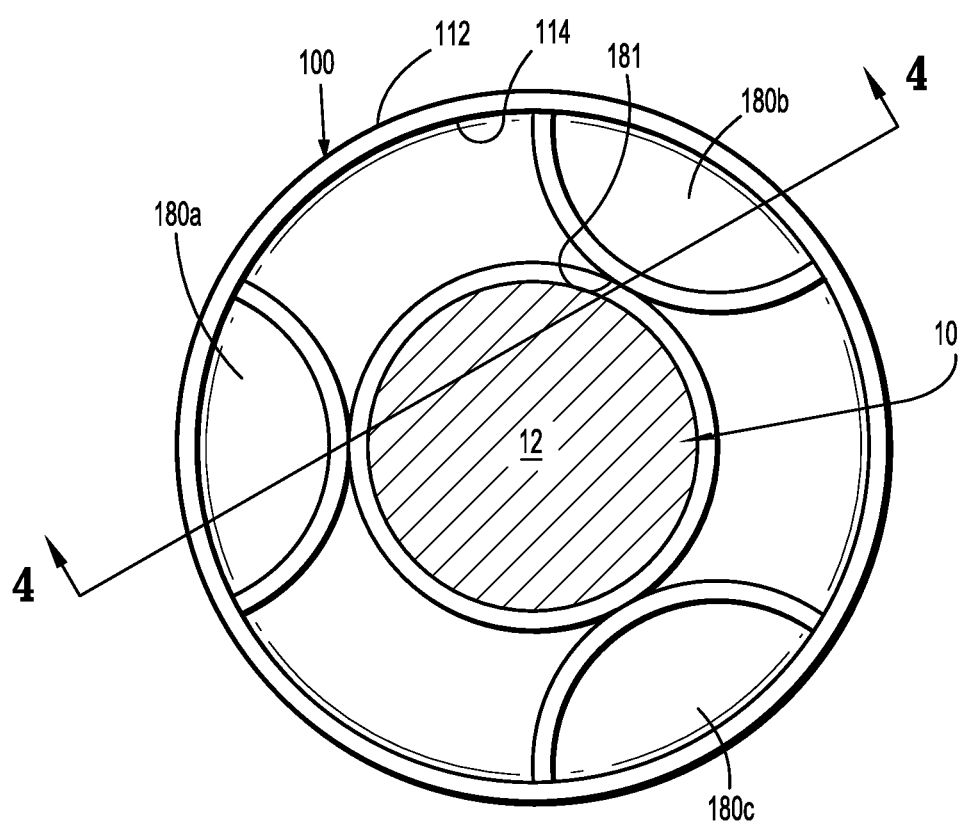
FIG. 3 is a top view of the port assembly of FIGS. 1 and 2 in accordance with embodiments of the present disclosure.
Figure 4:
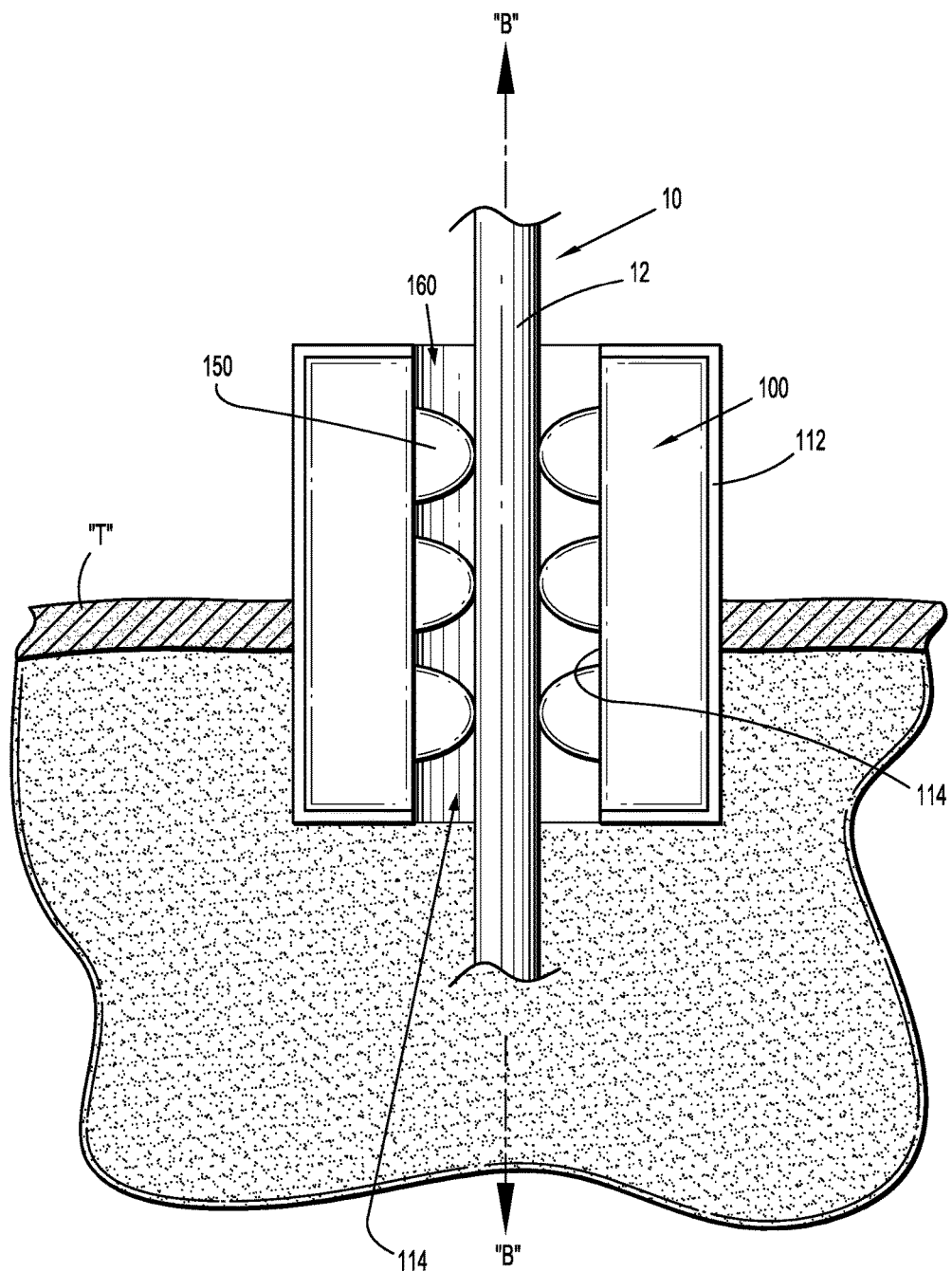
FIG. 4 is a cross-sectional view of the port assembly of the present disclosure, taken along line 4-4 of FIG. 3, shown with a surgical instrument extending longitudinally through an interior space therein.
Figure 5:
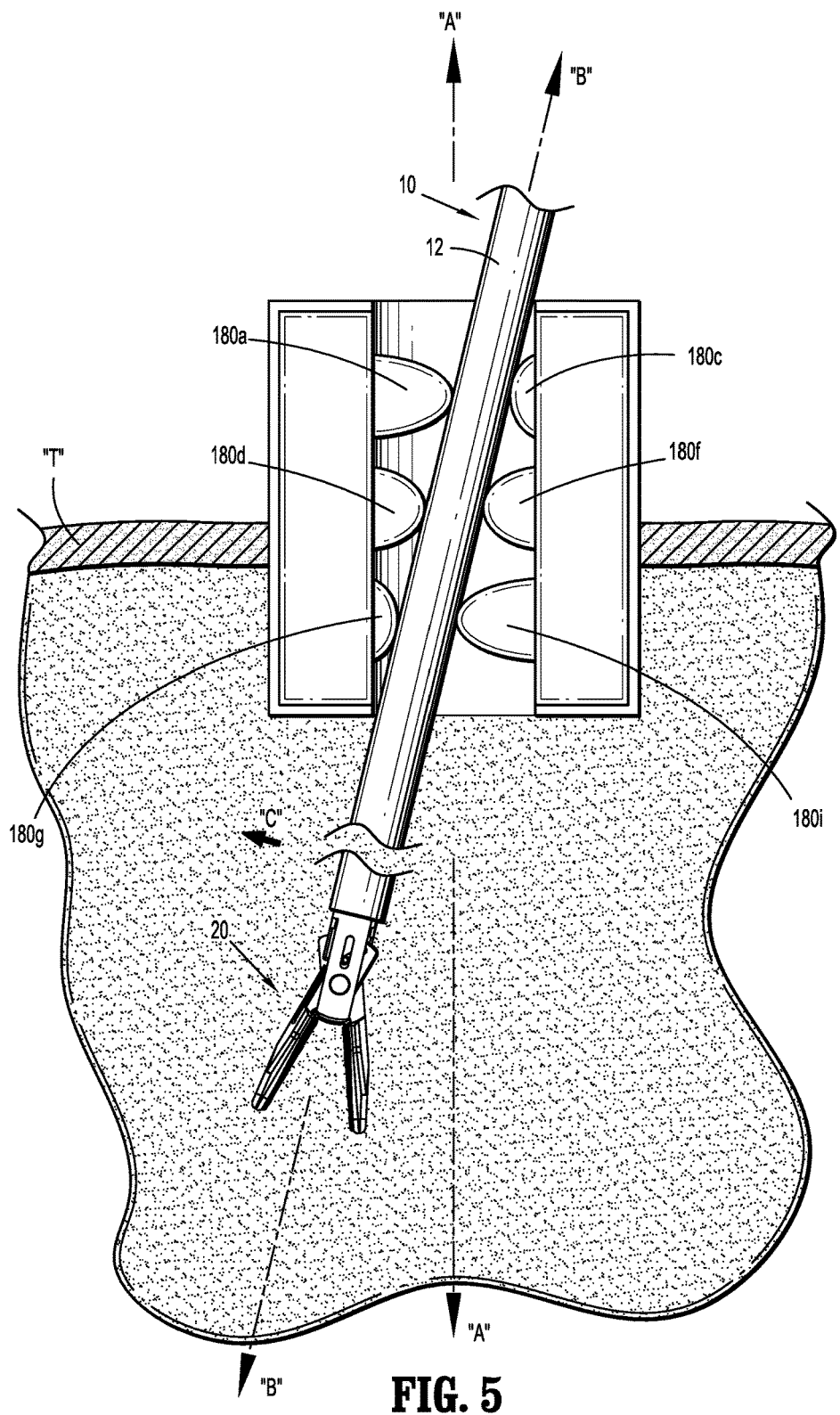
FIG. 5 is a cross-sectional view of the port assembly of FIGS. 1-4 shown with a surgical instrument extending through the interior space of the port assembly at an angle.

In the embodiment illustrated in FIG. 2, port assembly 100 includes nine inflatable members 180a-180i associated therewith. The inflatable members 180a-180i of the illustrated embodiment include a first, proximal row of three inflatable members 180a-180c radially disposed about interior surface 114 of the body 110, a second, middle row of three inflatable members 180d-180f radially disposed about interior surface 114 of the body 110, and a third, distal row of three inflatable members 180g-180i radially disposed about interior surface 114 of the body 110. As noted above, the amount, shape, size, arrangement, and orientation of inflatable members 180 are not limited by the accompanying figures. For example, more or fewer inflatable members are contemplated by the present disclosure.

Each inflatable member 180a-180i includes a respective conduit 182a-182i (FIG. 2) fluidly linking the inflatable member 180a-180i to the inflation medium 190. It is envisioned that inflation medium 190 is stored in individual storage containers (e.g., one storage container for each conduit 182a-182i), or that the inflation medium 190 is stored in a single storage container, and that each conduit 182a-182i includes a valve for controlling the amount of inflation medium 190 that can travel between the conduit 182a-182i and the respective inflatable member 180a-180i.

In use, endoscopic camera 200 is configured to view at least a portion of the end effector assembly 22 of the surgical instrument 10 within the body cavity. The sensor 210 is configured to store and/or relay information regarding the precise orientation and positioning of the end effector assembly 22 (e.g., the degree tilt of the shaft 12 with respect to the longitudinal axis "A," and the amount of rotation of the end effector assembly 22 about the longitudinal axis "B") within the body cavity with respect to the endoscopic camera 200. The sensor 210 is also configured to compare the current orientation and positioning information of the end effector assembly 22 with stored (e.g., initial, optimal, user-defined, etc.) orientation and positioning information.

The sensor 210 is further configured to communicate the orientation and positioning information of the end effector assembly 22 with control mechanism 300 including a controller. Moreover, the sensor 210 is configured to communicate the difference between the current orientation and positioning of the end effector assembly 22 with the stored (e.g., initial) orientation and positioning information. The control mechanism 300 is configured to distribute the inflatable medium 190 to the appropriate inflatable member(s) 180 in order to move the shaft 12 of the surgical device 10 to re-orient the end effector assembly 22, such that the end effector assembly 22 moves to its stored (e.g., initial) orientation and position. For example, and with particular reference to FIG. 5, to tilt the end effector 22 with respect to the longitudinal axis "A" in the general direction of arrow "C," inflatable members 180a and 180i could be inflated and/or inflatable members 180c and 180g could be deflated. (Inflatable members 180b, 180e and 180h are not shown in FIG. 5 due to the particular cross-sectional view illustrated.)

Additionally, it is envisioned that rotation of the elongated shaft 12 about the longitudinal axis "B" could be accomplished by sequential inflation and/or deflation of adjacent inflatable members 180 (e.g., inflatable members 180 that are axially-aligned and radially-adjacent). For instance, rotation of the elongated shaft 12 may be accomplished by first inflating inflatable member 180a a certain amount (e.g., by a particular volume and/or a particular duration) while deflating inflatable member 180b, then inflating inflatable member 180c while deflating inflatable member 180a, then inflating inflatable member 180b while deflating inflatable member 180c. Additionally, it is envisioned that radially-aligned and axially-offset inflatable members (e.g., 180a, 180d and 180g; 180b, 180e and 180h; and 180c, 180f and 180i) can be inflated and/or deflated concurrently to facilitate rotation of the elongated shaft 12 about longitudinal axis "B."

It is envisioned that a user is able to set various parameters using the control mechanism 300. For example, it is envisioned that a user is able to set an initial orientation and position of end effector assembly 22 (e.g., after end effector assembly 22 is desirably positioned within the body cavity) via touch screen or pressing a button on the surgical device 10 and/or the control mechanism 300, for example. It is further envisioned that a user can select whether the control mechanism 300 changes the orientation and position of the end effector assembly 22 continuously (i.e., continuously ensuring the current orientation and position of the end effector assembly 22 matches the initial orientation and position), intermittently (i.e., changing the orientation and position of the end effector assembly 22 after a given amount of time, if necessary, such that the current orientation and position of the end effector assembly 22 matches the initial orientation and position), based on amount of movement of the end effector assembly 22 from its initial position (i.e., changing the orientation and position of the end effector assembly 22 after the end effector assembly 22 has moved a predetermined amount from its initial position), and/or at user-defined times (e.g., after removal and re-insertion of the surgical instrument 10 or a different surgical instrument), for example.

It is further envisioned that control mechanism 300, or another portion of the surgical system 5, is configured to give feedback to a user corresponding to a particular amount of change in position and/or orientation of the end effector assembly 22 of the surgical instrument 10. For example, it is envisioned that surgical system 5 gives visual (e.g., illuminating a light), audible (e.g., producing a beeping sound), and/or tactile (e.g., causing a handle of the surgical instrument 10 to vibrate) feedback in response to the change of position and/or orientation of the end effector assembly 22 which exceeds a predetermined value. Upon receiving this feedback, the user may manually instruct (e.g., by pushing a button) the control mechanism 300 to reposition the surgical instrument 10 back to its initial position and orientation, for example.

The present disclosure also comprises the inclusion of a friction-enhancing surface or coating on an instrument-engaging surface 181 (see FIG. 3) of at least one (e.g., all) inflatable member 180. It is envisioned that the friction-enhancing surface 181 is made from a material that is different from another portion of the inflatable member 180. For example, a majority of each inflatable member 180 may be made from, and the friction-enhancing surface or coating may include.

In use, it may be desirable to insert and/or position the surgical instrument 10 when inflatable members 180 are at least partially deflated, and then to inflate necessary inflatable members 180 to help secure the location, position and orientation (e.g., initial position) of the surgical instrument 10.

System 5 of the present disclosure may include a storage device. The storage device may include a set of executable instructions for performing a method of controlling surgical instruments using a port assembly 100 as described herein. In some embodiments, the system 5 also includes a processing unit and/or a database. Further details of exemplary processing units and databases are described in U.S. Pat. No. 8,641,610, which has been incorporated by reference hereinabove.

The present disclosure also includes methods of controlling surgical instruments using system 5, or portions thereof, as described above. It is to be understood that the features of the method provided herein may be performed in combination and in a different order than presented herein without departing from the scope of the disclosure.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 6:
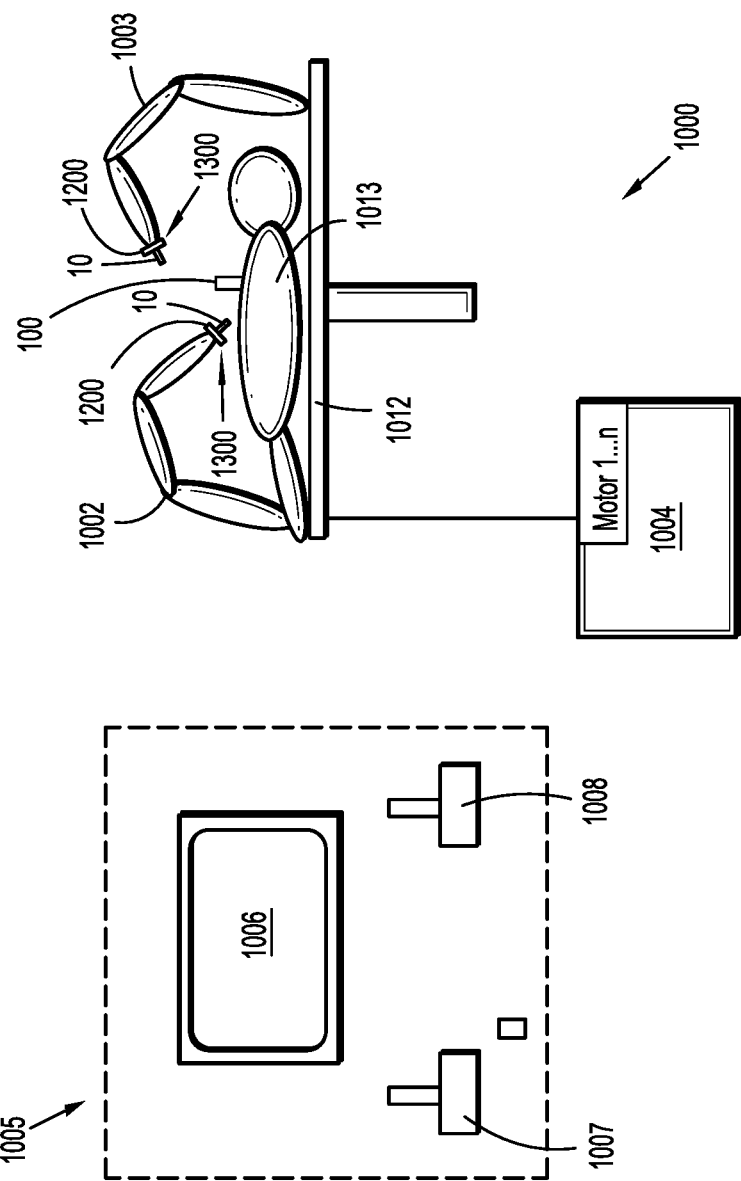
FIG. 6 is a schematic illustration of a surgical system in accordance with the present disclosure.
Figure 8:
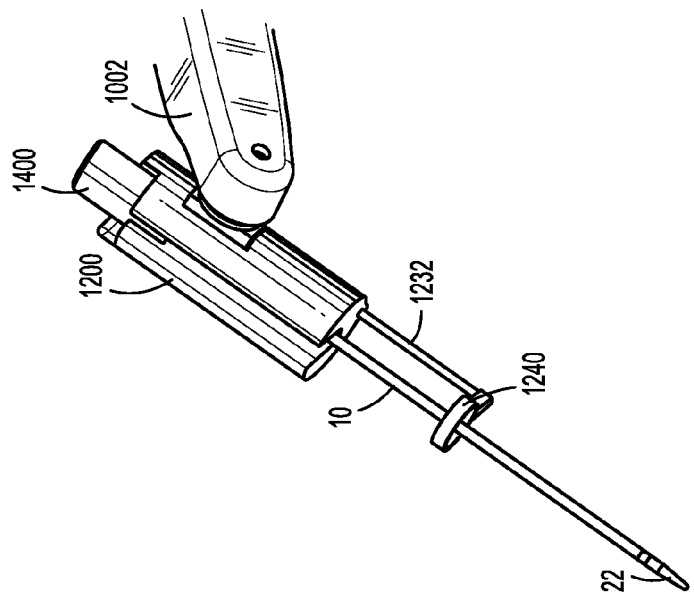
FIG. 8 is an enlarged view of the surgical assembly of FIG. 7, shown extended through a guide ring.
Figure 7:
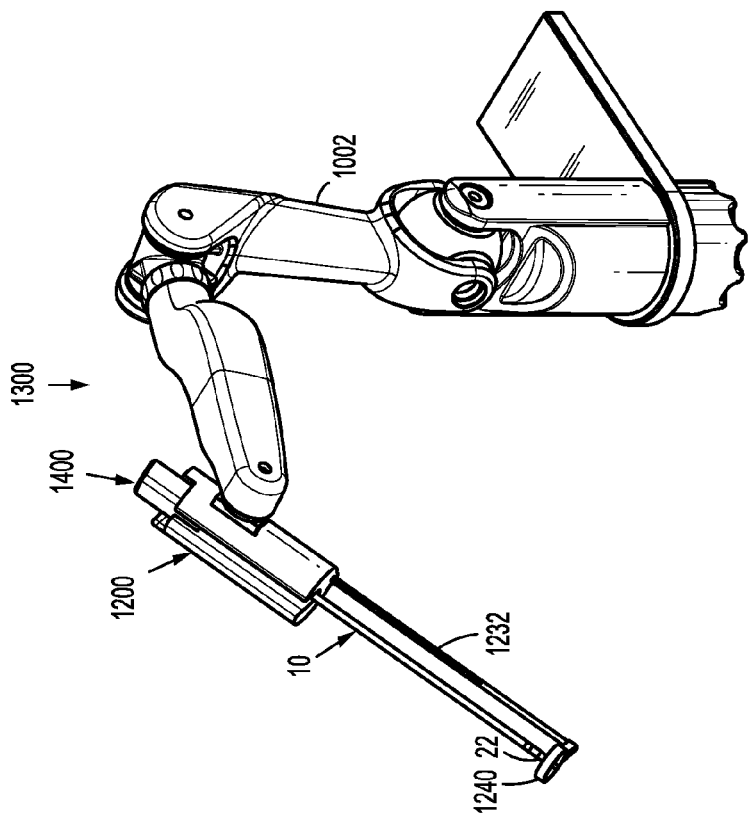
FIG. 7 is a perspective view of a surgical assembly in accordance with an embodiment of the present disclosure illustrated being attached to robot arms of a robotic surgical system.

With reference to FIGS. 6-8, a surgical system, such as, for example, a robotic surgical system is shown generally as surgical system 1000 and is usable with surgical system 5, or portions thereof, of the present disclosure. Surgical system 1000 generally includes a plurality of robotic arms 1002, 1003, a control device 1004, and an operating console 1005 coupled with control device 1004. Operating console 1005 includes a display device 1006, which is set up in particular to display three-dimensional images; and manual input devices 1007, 1008, by means of which a person (not shown), for example a surgeon, is able to telemanipulate robotic arms 1002, 1003 in a first operating mode, as known in principle to a person skilled in the art.

Each of the robotic arms 1002, 1003 is composed of a plurality of members, which are connected through joints. System 1000 also includes an instrument drive unit 1200 connected to distal ends of each of robotic arms 1002, 1003. Surgical instrument 10 supporting end-effector assembly 22 may be attached to instrument drive unit 1200, in accordance with any one of several embodiments disclosed herein, as will be described in greater detail below.

Robotic arms 1002, 1003 may be driven by electric drives (not shown) that are connected to control device 1004. Control device 1004 (e.g., a computer) is set up to activate the drives, in particular by means of a computer program, in such a way that robotic arms 1002, 1003, their instrument drive units 1200 and thus the surgical instrument 10 (including end-effector assembly 22) execute a desired movement according to a movement defined by means of manual input devices 1007, 1008. Control device 1004 may also be set up in such a way that it regulates the movement of robotic arms 1002, 1003 and/or of the drives.

Surgical system 1000 is configured for use on a patient 1013 lying on a patient table 1012 to be treated in a minimally invasive manner by means of end-effector assembly 22. Surgical system 1000 may also include more than two robotic arms 1002, 1003, the additional robotic arms likewise being connected to control device 1004 and being telemanipulatable by means of operating console 1005. A surgical instrument 10 (including end-effector assembly 22; see FIGS. 7 and 8) may also be attached to the additional robotic arm.

Reference may be made to U.S. Patent Publication No. 2012/0116416, filed on Nov. 3, 2011, entitled "Medical Workstation," the entire content of which is incorporated herein by reference, for a detailed discussion of the construction and operation of surgical system 1000.

Turning to FIGS. 7 and 8, surgical system 1000 includes a surgical assembly 1300, which includes robotic arm 1002, an instrument drive unit 1200 connected to robotic arm 1002, and surgical instrument 10 coupled with or to instrument drive unit 1200. Instrument drive unit 1200 is configured for driving an actuation of end-effector assembly 22 of surgical instrument 10 and to operatively support surgical instrument 10 therein. Instrument drive unit 1200 transfers power and actuation forces from motors "M" to surgical instrument 10 to ultimately drive movement of cables that are attached to end-effector assembly 22, for example.

In use, a trocar shaft 1232 is moved between a pre-operative position, as shown in FIG. 7, and an operative position, as shown in FIG. 8. In the pre-operative position, a guide ring 1240 and end-effector assembly 22 are coplanar. In the operative position, guide ring 1240 is located proximal to end-effector assembly 22.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical port assembly for use with surgical instruments, the surgical port assembly comprising:
   a body including an exterior surface and an interior surface, the interior surface defining an interior space, the interior space configured to allow a surgical instrument to pass therethrough; and
   a control interface including a plurality of inflatable members coupled to the body and inflatable to selectively apply a force to a portion of a shaft of the surgical instrument when the shaft is disposed within the interior space, wherein each of the plurality of inflatable members is independently selectively inflatable to move a distal portion of the surgical instrument to a desired position.

2. The surgical port assembly according to claim 1, wherein at least one of the plurality of inflatable members is configured to apply a force to the surgical instrument in a direction perpendicular to a longitudinal axis of the body.

3. The surgical port assembly according to claim 1, wherein at least one of the plurality of inflatable members includes a friction-enhancing material.

4. The surgical port assembly according to claim 3, wherein a majority of each inflatable member is made from a first material, and wherein the friction-enhancing material is different from the first material.

5. The surgical port assembly according to claim 1, wherein the plurality of inflatable members includes nine inflatable members.

6. The surgical port assembly according to claim 5, wherein the nine inflatable members include a first set of three axially-aligned inflatable members, a second set of three axially-aligned inflatable members, and a third set of three axially-aligned inflatable members.

7. The surgical port assembly according to claim 5, wherein the nine inflatable members include a first set of three radially-aligned inflatable members, a second set of three radially-aligned inflatable members, and a third set of three radially-aligned inflatable members.

8. A surgical system, comprising:
   a surgical port assembly including a body and a control interface, the body including an exterior surface and an interior surface, the interior surface defining an interior space, the interior space configured to allow a surgical instrument to pass therethrough, the control interface including a plurality of inflatable members coupled to the body and inflatable to selectively apply a force to a portion of a shaft of the surgical instrument when the shaft is disposed within the interior space, wherein each of the plurality of inflatable members is independently selectively inflatable to move a distal portion of the surgical instrument to a desired position;
   an endoscopic camera, a portion of the endoscopic camera being positionable within a body cavity and configured to view the distal portion of the surgical instrument; and
   a control mechanism disposed in operative engagement with the surgical port assembly and the endoscopic camera, the control mechanism configured to control inflation and deflation of the plurality of inflatable members.

9. The surgical system according to claim 8, wherein the control mechanism is configured to control inflation and deflation of each the plurality of inflatable members in response to information received from the endoscopic camera.

10. The surgical system according to claim 8, further comprising an inflation medium disposed in fluid communication with each of the plurality of inflatable members individually.

11. The surgical system according to claim 10, wherein the inflation medium is disposed in operative communication with the control mechanism.

12. The surgical system according to claim 8, wherein at least one of the plurality of inflatable members includes a friction-enhancing material.

13. The surgical system according to claim 12, wherein a majority of each inflatable member is made from a first material, and wherein the friction-enhancing material is different from the first material.

14. The surgical system according to claim 8, wherein the plurality of inflatable members includes nine inflatable members.

15. The surgical system according to claim 14, wherein the nine inflatable members include a first set of three axially-aligned inflatable members, a second set of three axially-aligned inflatable members, and a third set of three axially-aligned inflatable members.

16. The surgical system according to claim 14, wherein the nine inflatable members include a first set of three radially-aligned inflatable members, a second set of three radially-aligned inflatable members, and a third set of three radially-aligned inflatable members.

* * * * *